United States Patent [19]

Tse

[11] Patent Number: 4,662,228
[45] Date of Patent: May 5, 1987

[54] AUTOMATED INTERFACIAL TESTING SYSTEM

[75] Inventor: Ming K. Tse, Lake Jackson, Tex.

[73] Assignee: The Dow Chemical Company, Midland, Mich.

[21] Appl. No.: 818,577

[22] Filed: Dec. 27, 1985

[51] Int. Cl.[4] ............................................. G01N 21/00
[52] U.S. Cl. ......................................... 73/842; 73/827
[58] Field of Search ................... 73/827, 821, 81, 842; 350/531

[56] References Cited

U.S. PATENT DOCUMENTS 2,420,654 5/1947 Cohen et al. ............................ 73/81

OTHER PUBLICATIONS

Giedd, G. R., Precision X-Y Table, IBM Technical Disclosure Bulletin, vol. 13, No. 6, Nov. '70.
Grande, D. H., Fiber/Matrix Interface in Composite Materials, MIT Master's Thesis, May 6, 1983, pp. 2,4,6,20,21,35-37,91,99,100-102.

Primary Examiner—Jerry W. Myracle
Attorney, Agent, or Firm—J. G. Carter

[57] ABSTRACT

For use in inspecting composite materials made of fibers in a supportive polymer matrix, a test instrument and method are set forth. The apparatus uses an optical microscope to provide a view of a cut specimen having small fibers therein. The optical axis through the microscope defines an arbitrary location. In x and y dimensions, at an offset of m and n from the optical axis, a stylus having a tip is located. Through the use of stepping motors connected through appropriate gear boxes, the stage supporting the specimen is moved. This locates a particular fiber previously positioned coincident with the optical axis so that it can be tested. Testing is accomplished by moving through the offset distances of m and n to position the stylus tip over the particular fiber. On movement in the z axis, the tip is embedded in the fiber to test bonding.

20 Claims, 5 Drawing Figures

AUTOMATED INTERFACIAL TESTING SYSTEM

BACKGROUND OF THE DISCLOSURE

The present disclosure is directed to a testing device. It is a device especially to be used for testing the bond between fibers and supportive polymer bodies surrounding the fibers. A typical device made of composite materials is a fly rod. Fibers are arranged parallel to one another and are bonded together into a composite body by placing a resin polymer matrix around the fibers. The fibers and resin are shaped to the final shape. The fibers can be made of many materials. For instance, fiber glass is a popular fiber. It is relatively large in comparison with carbon fibers. Carbon fibers are relatively small, one of the smallest fiber of commercial interest. The measurements for the fibers may vary but it is not uncommon for fibers in composite materials to be in the range from about 5 to about 250 microns diameter. The quality of the composite article of manufacture is in part determined by the bond between individual fibers and the surrounding matrix. This bond is the location at which failure may occur. In fact, the grip between the matrix and the fiber in the matrix is an important factor in providing a high quality article of manufacture utilizing composite materials.

One mode of testing such a device is to attempt to push or pull the fiber to determine breaking of the bond between the fiber and the supportive matrix. With fibers as small as 5 microns diameter, this is extremely difficult to do. Moreover, because there are so many fibers in a typical manufactured article, it is essential to test many fibers. Going back to the example of a fly rod and utilizing graphite fibers having a typical diameter of about 5 or 6 microns, the cross section of the fly rod even at the narrow tip areas may well include over 100,000 fibers. It would not be uncommon to have as many as one million fibers arranged more or less parallel to one another structurally supporting a composite article of manufacture. For this reason, it is important to test many fibers. This provides a statistical data base which enables compiling of meaningful data as opposed to data regarding the bond between a single fiber and the surrounding matrix.

The apparatus of this disclosure is a system enabling testing of individual fibers. Across a cast body made of composite materials (that term shall be applied hereinafter to a set of parallel fibers adhesively held together with a surrounding cured matrix), a transverse cut is made to define an exposed face. This exposed face is ideally perpendicular to the fibers. At least, the bulk of the fibers should be approximately perpendicular to the face. The face is preferably mechanically polished and smoothed so that the cut ends of the various fibers intersected by the face maintain their nominal size and shape. A stylus featuring a small tip or point is pressed against the end of a fiber. While it is easy to describe this in general terms, there is a great deal of difficulty because the stylus is far larger than a single fiber and the point of contact of a particular stylus against the face (intersecting 100,000 or more fibers) is difficult to ascertain. The data proves nothing if the point of the stylus strikes against the matrix. Moreover, it does not really prove much if the point of the stylus contacts a fiber at the edge of the fiber, meaning the interface between fiber and matrix. Rather, the ideal approach is that the tip of the stylus contact the fiber at the center of the fiber. It is rather difficult to line up a large stylus and position the tip of the stylus at the precise center of a fiber which is only 5 or 6 microns in diameter.

The present apparatus approaches this problem by arranging an optical microscope system which looks at the sample supported on a stage in the microscope system which is movable in x, y and z dimensions. Optical system microscopes able to properly focus on and provide an image of the tips of fibers measuring only 5 microns in diameter are available. Such an optical system, of course, requires a fairly large lense system, extremely large in contrast with the diameter of the fiber undergoing testing. In fact, it can be reasonably said that the lense is perhaps thousands of times greater in diameter than the fiber which is being viewed through the lense. Moreover, the lense must be arranged parallel to the face of the specimen so that it can view the end of the fiber. At this juncture, it must not only be parallel but relatively close. This precludes inserting any kind of instrument in the gap between the lense and the test specimen. Even if an instrument could be inserted in that region, it would so obscure the optical view that one could not know precisely where the instrument was located, at least with the accuracy sufficient to land the tip of the inserted instrument precisely at the center of an optical fiber. Restated, this simply recognizes the fact that the test instrument (a pointed stylus) is so large that its insertion would obscure the optical system whereby the instrument tip is located. If the tip cannot be located, there is no certainty that it contacts the matrix or fiber; it simply will contact something at some location on the face. Even that is not sufficient by hindsight inspection looking for the dimple or indention formed by the previous use of a pointed instrument. The reason that post testing inspection is not possible is that the instrument may contact the face to form an indention of perhaps 1 or 2 microns diameter which is simply too small to be located by post dimpling inspection.

The present apparatus suggests a system for overcoming these and other handicaps. The system utilizes an optical microscope system so that an observer can view the cut specimen through the optical system. The field of view is perpendicular to the face of the specimen. Through the use of conventional optical cross hairs, a particular point in the target area can be located. The stage can be adjusted in position to obtain a sharp focus and also to locate the cross hair intersection over a particular fiber. Once this has been accomplished, a particular fiber being designated, the next step in use of the apparatus is then to position the stylus at the location at the cross hair. The stylus, having a shaped tip thereon, is then moved into the location where the cross hair intersection once was located. To this end, the optical axis through the microscope system defines what might be termed a reference axis. This reference axis is used as a means of determing an origin in an x-y system. The optical system thus defines the origin or the point of 0,0. Off to the side at some measure known by x and y coordinates, a parallel positioned stylus is located. The distance between the axis of the stylus and the optical system is a specific measure. This measurement can be determined to an accuracy of less than one micron in x and y dimensions. In this arrangement, the stylus is made parallel to the optical axis. It is offset by a specific distance. This distance will be represented hereinafter as the measurements of m and n which are offsets measured in microns from the origin of the x-y plane and which is coincident with the optical axis. The values of m and n are fixed on manufacture of the apparatus. Thus, a particular stylus is installed and mounted so that it is parallel to the axis through the origin. The tip is located at a distance known by m and n from the origin. These measurements are determined in microns in the preferred embodiment. This offset (m and n) is stored in memory for subsequent translation. The tip of the stylus is located at a vertical location or z position. This tip is located so that it is several thousand microns above the face of the specimen when the specimen is viewed optically. That is, the lense system is placed a specified height above the sample so that a proper focus can be determined. This positions the tip in space several thousand microns above the face of the specimen. At the time that a test is undertaken, the tip is first moved to the previously established cross hair location by adjustment of the x-y stage through the distances of m and n. Once this is accomplished, the tip of the stylus is then lined up with the particular cross hair location previously observed visually. At that juncture, using movement along the z axis, the tip of the stylus is brought in contact with the specimen with the assurance that it strikes the specimen at a predetermined location. After testing in a fashion to be described, the indention at that particular cross hair location can then be inspected visually to be sure that the test has been completed. Moreover, the break in the bond, if any, can be visually inspected to make qualitative determinations regarding the bond holding the components of the composite material together.

The present apparatus is therefore summarized as an optical system which has an optical eye piece to be viewed while supporting an objective lens positioned above a sample holder. The sample holder is supported on an x-y-z stage which is driven by x-y-z stepping motors connected to appropriate gear drive systems. Conveniently, the optical system also includes a video camera and a mounting for a still camera. The optical lense system defines an optical axis or an origin on x, y coordinates at 0,0. An offset stylus is located at a distance of m and n from the origin at 0,0. This measure if fixed at the time of manufacture and installation of the particular stylus. The offset measurements of m and n are stored in memory. The memory controls a drive signal for stepping motor drivers. When the motors are driven, thereby traversing the stylus tip to the point coincident with the optical axis or the origin at 0,0, and a test can be made. The device also includes means for traversing in the z direction. A load cell measures loading, and travel in the z direction is also measured, thereby enabling a measurement of a stylus tip penetration into the composite material. The stylus tip enters at the specified location determined by optical inspection and aligned with the cross hair in the optical system.

DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
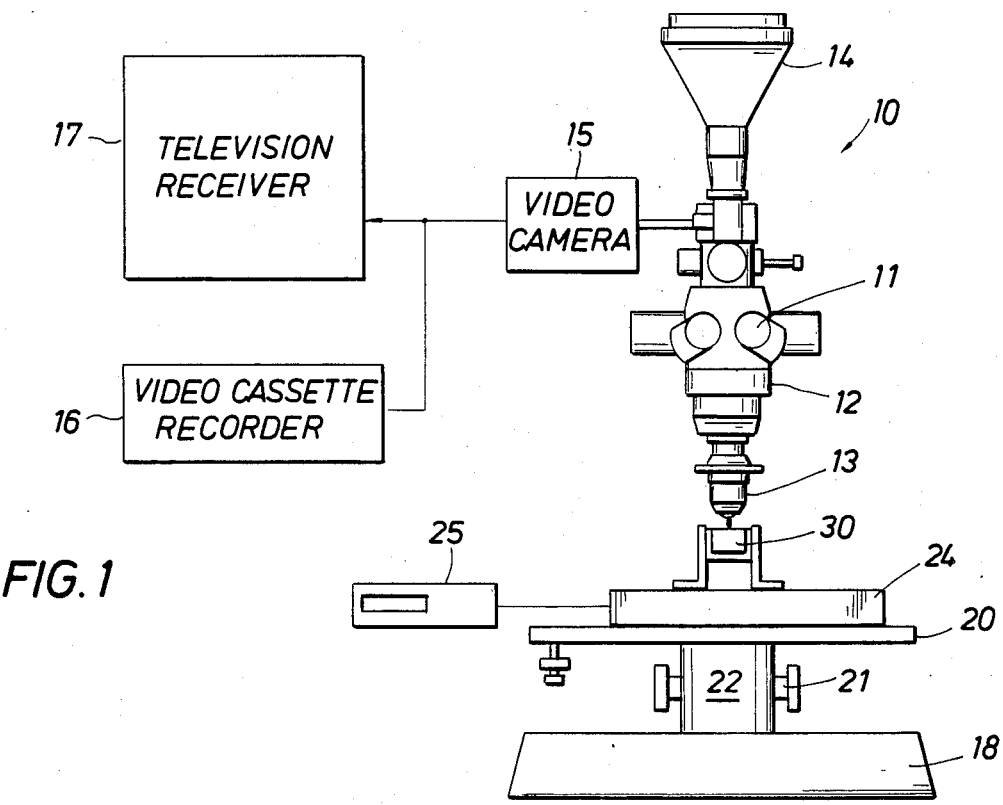
FIG. 1 shows the interfacial testing apparatus of the present disclosure and particularly shows an arrangement of an optical microscope system with a x-y stage.

Attention is directed to FIG. 1 of the drawings. There, the apparatus identified by the numeral 10 will be described in general terms after which specific features will be discussed. The system includes an eye piece 11 for binocular viewing of an optical microscope 12. The operator is able to see through the eye piece 11 and an objective lens 13. The objective lens 13 is mounted on the microscope in the conventional fashion. The system is equipped with a cross hair. The measure of a magnification is sufficient that a five micron fiber in cross-section is sufficiently large that the cross hair can be accurately centered on the fiber. Such a microscope is available from commercial sources and one typicl source is Zeiss Company, West Germany. By means of various optional features available from that firm and through the selection of appropriate lenses offered by that firm, the optical system is capable of forming high resolution images over a range of magnification. The device includes a mounting for a still camera 14, and an image splitter is included which provides air image for a video camera 15. The video camera is connected with a video cassette recorder at 16. Likewise, it is connected with a television receiver at 17 to provide a large dynamic image of the field of view.

The optical system is placed above a base 18. The base supports an x-y stage 20. The stage 20 is driven in two dimensions, hereinafter identified as x and y dimensions, by means of a stepper motor 21 which drives a gear box 22 interposed between the motor and the stage. Thus, the motor rotates incrementally to drive the stage by a measured amount. The gear box provides gearing to a suitable ratio. A typical stepping motor is manufactured by Superior Manufacturing Company. Various ratios can be obtained including stepping motors which provide 20, 200 and 360 steps per revolution. The stepping motor increment of rotation is matched with the gear box so that the stage moves specified distance per step. Stage increments as small as about 0.25 microns can be obtained. For convenience, the system will be described as having a stepping motor and gear box combination which provides steps of 1.0 microns per operation. That is, each operation or increment of movement is best movement in the micron range. Smaller increments can be obtained. The device is operated with a high measure of reliability to thereby locate the cross hairs in the optical system at measurements accurate to 1.00 micron with a margin of error of less than about 0.25 microns.

The stepping motor 21 is provided for movement in one dimension and similar, even identical, stepping motor and gear box arrangement are used to translate in the second and third dimensions. The stage 20 is mounted so that it can travel in x and y dimensios. This permits lateral translation to locate a particular fiber in the sample holding system as will be described. Movement along the z axis is accomplished in the same way by an identical stepping motor connected to an identical gear box. The x-y-z coordinate system supporting the sample (to be described) is an arrangement such that three dimensional movement can be obtained with measurement of 1.0 microns and with an accuracy sufficient to obtain this type of measurement.

The stage 20 supports a load cell 24. The load cell is connected with a load cell output circuit at 25. This provides a digitized measurement of the load. The load is measured in micrograms.

Figure 2:
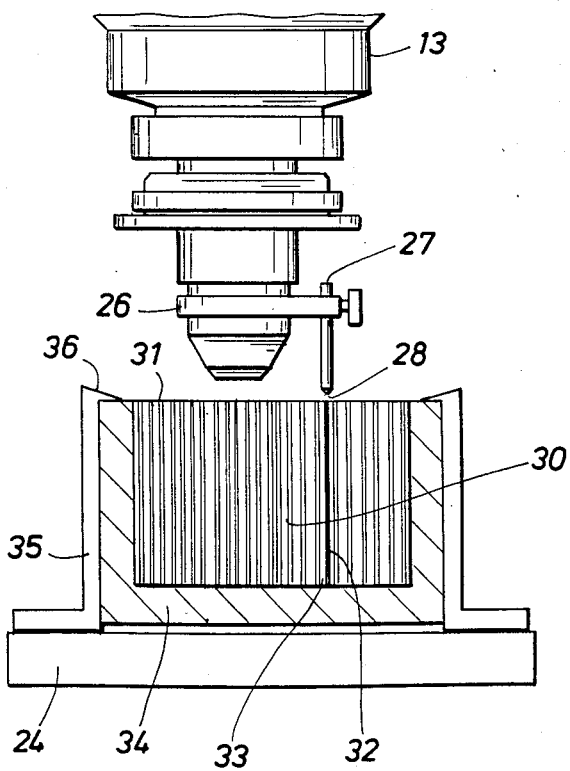
FIG. 2 is an enlarged detail view showing the optical lens system positioned above a composite material sample and shows lateral mounting of a stylus to be positioned for testing of the bond between an individual fiber and the supporting polymer matrix.

Attention is now directed to FIG. 2 of the drawings. This enlarged view again illustrates the objective lens 13. This lens system is constructed with a cross hair coincident with the optical axis. It supports a fixed clamp or collar 26. The collar fastens an upstanding stylus 27. The stylus incorporates a diamond tip at 28. The tip is small, in the range of a fraction of a micron. It is on a tapered cone at the lower end of the stylus. It is fixed in location at the time of installation. The location of the stylus locates the tip at the distance of m and n from the optical axis. Moreover, it has an axis which is parallel to the optical axis. The tip is located below the objective lense system. By this construction, the diamond tip 28 can be moved to a location coincident with the optical axis so that movement along the z axis contacts the tip 28 against the sample.

In FIG. 2, a sample 30 is positioned for inspection. It has an exposed upper face 31. This face is preferably perpendicular to the optical axis. Preferably, the fibers in the composite materials are also perpendicular to the face. The numeral 32 identifies a single fiber. It is held in the composite material formed by a polymer matrix 33. While there is a single fiber tested individually, there are typically multiple thousands of fibers. The fibers are intersected by the face 31, cut transverse by that face and are individually tested. Each fiber is gripped by the polymer matrix 33 which surrounds the fiber. In the event the specimen is too small, it is surrounded with a potting agent 34 which is cast around it. This enables the specimen to fit in a sample holder 35. The sample holder 35 is a surrounding ring formed with an upstanding wall and having a lip 36 at the top to fasten the sample or specimen at a specified location. This enables testing of uniform size samples, the potting agent being added to increase the bulk of the structure for testing. All of this is placed on the load cell 24 which is sensitive to loading from the stylus. The load cell is zeroed supporting the apparatus shown in FIG. 2. The weight is zeroed prior to contact of the tip 28 against the specimen 30.

Figure 3:
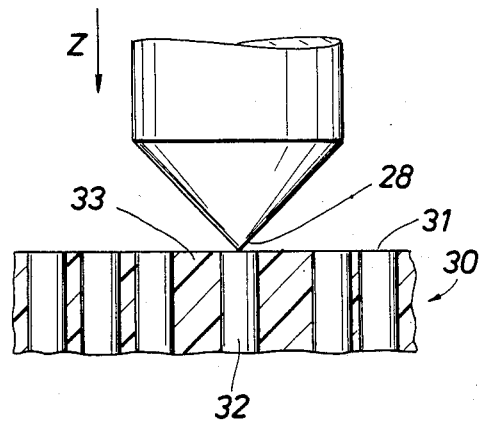
FIG. 3 is a view further enlarged compared with FIG. 2 showing the tip of the stylus positioned above a fiber for testing the interfacial bond between the particular fiber and the surrounding matrix.

Going now to FIG. 3 of the drawings, the individual fiber 32 is tested by contact of the tip 28 against it. The tip is made quite small, tapering to a conic point. The tip is a sharp instrument sufficiently small that a fiber of five micron diameter is indented only at the center when the tip first contacts. The area of initial contact is quite small, only a fraction of a micron. The stylus travels in the z direction. Such movement is accomplished by raising the stage which supports the specimen. This travel causes the tip 28 to embed in the specimen, and more particularly tends to separate the fiber, breaking the bond between the fiber and the polymer. This is a circular bond. The fiber tends to slide when the bond is broken. Typically, there will be a change in loading with penetration, thus, the load increases as the tin 28 penetrates the face 31. When the fiber breaks the bond, there is slippage in the system. This is reflected by change in loading as measured at the load cell.

Figure 4:
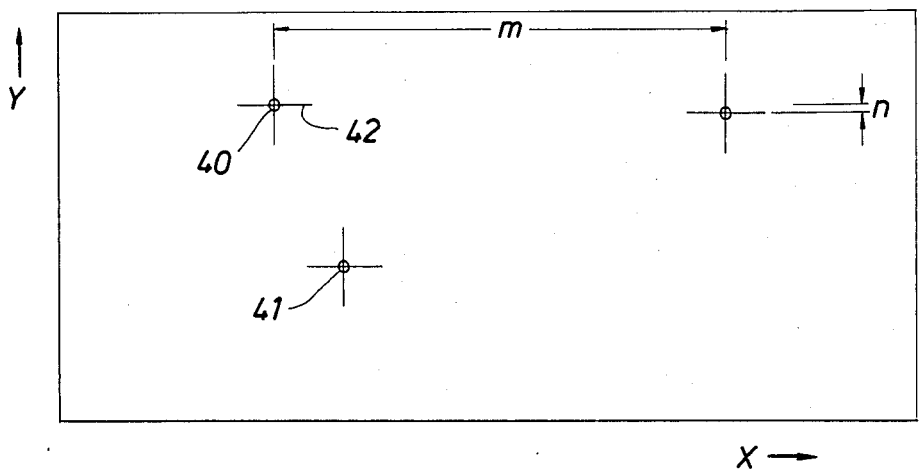
FIG. 4 shows an x-y coordinate system in graph form locating various fibers thereon and showing the offset m and n between the optical axis of the microscope system and the tip of the stylus.

Going now to FIG. 4 of the drawings, two arbitrarily located fibers are shown. The first fiber is identified by the numeral 40. A second fiber is located at 41. The apparatus is positioned above the sample or specimen so that the cross hairs represented at 42 are located and centered over the fiber 40. At this point, the fiber 40 is in view of the operator. The operator can not only see but the fiber can interpose the cross hairs over the optical image so that the cross hairs intersect at the center of the fiber. The scale is sufficient that the cross hairs intersect in the center of the fiber 40. Thereafter, and assuming a sharp focus, the system is operated to move the tip 28 so that it coincides with the location of the cross hairs 48. This is acomplished by relatively interchanging stylus over the optical axis. It is possible to move the optical system. However, it is preferable to hold it at a fixed location and move the stage, thereby moving the sample 30. The stage is translated by the distances of m and n represented in FIG. 4. So to speak, the tip 28 is off to the side of the cross hair coincident with the optical axis. This movement of m and n measure is accomplished by translation in the x and y axis. The stepping motors are operated, providing movement to the respective gear boxes so that the test sample 30 is moved beneath the microscope. The distances m and n are known accurately because they are fixed at the time of manufacture and assembly of the equipment shown in FIG. 2. This fixed offset distance (m and n) is dependent on the construction of the apparatus and is fixed after construction. Thus, the distances m and n are stored in memory (to be described below) and the specimen 30 is moved to the distance m and n. This then locates the tip 28 above the individual fiber 40 in the fashion shown in FIG. 3. After testing, the stage can be moved back to locate the cross hairs 42 over the fiber 40, this being done by reversing the movement, previously accomplished. In other words, the stage is moved along the x and y dimensions by the distances of -m and -n. It will be recognized that the offsets m and n carry a sign dependent on the definitions of the sytem, namely location of the origin and the arbitrary assignment of positive and negative in the x-y coordinate system. The dimple made at the fiber 40 can then be inspected. This is extremely important in view of the fact that the sample typically will include in excess of 100,000 fibers.

A second fiber is shown at 41. After the fiber 40 has been first located, then tested, thereafter inspected visually to evaluate the debonding which occurs in testing, the system can then be operated to located the fiber 41. The cross hair is located over the fiber 41 to initiate a second test. Multiple tests can obviously be carried out with any of the multiple fibers available for testing. To this end, FIG. 4 is simplified in that only two fibers are shown while there is in actuality multiple of thousands fibers available for testing.

Figure 5:
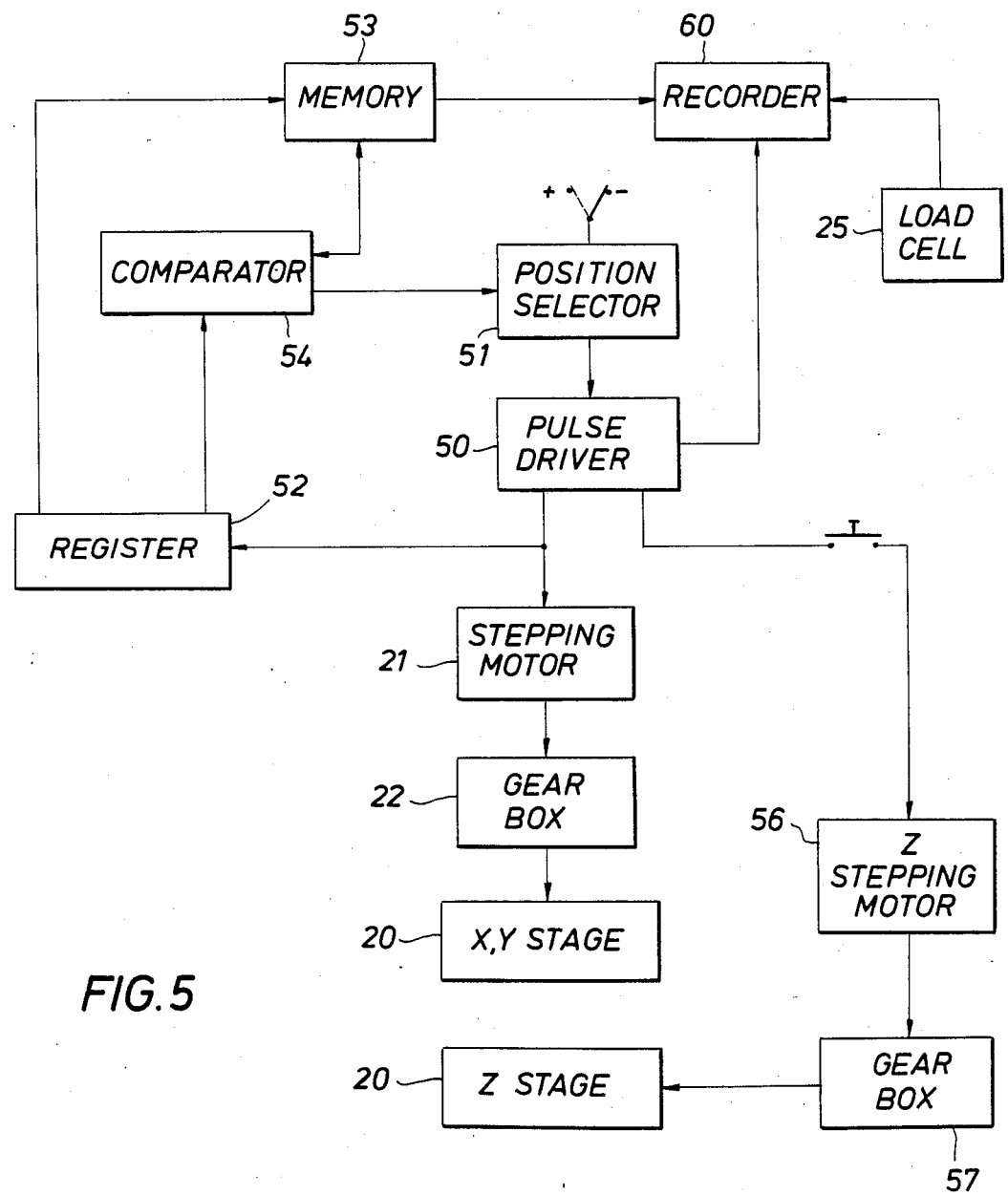
FIG. 5 is a block diagram schematic of a control system for the optical testing instrumentation.

Attention is now directed to FIG. 5 which shows a system for operation of the stepping motors. Recall that a stepping motor is included in FIG. 1 at 21. A single stepping motor is shown in FIG. 5. Of course, three stepping motors are used, one for each dimension. Stepping motor 21 drives a gear box 22. The gear box is then connected to the stage 20 which is translated in x and y dimensions. X and y operation are separated from the description of movement in the z direction. The stage is moved through the necessary distances, the distances being m and n. The stepping motor 21 is driven by a pulse driver 50. The pulse driver 50 forms a sequence of pulses of specified number to accomplish the necessary movement. The pulse driver is triggered in operation by a position selector 51. The position selector starts the pulse driver circuit 50 in operation. It is connected with a digital register 52. The register 52 stores a numeric evaluation of the location of the stage in a particular dimension. The register 52 preferably counts up and down. The beginning point is stored in a memory 53. This might be in reference to some arbitrary location, therebeing no particular need to reset the system to zero after each operation. At any point, the location of the stage is known in each of three dimensions. Thus, the memory 53 records the location of the stage. When it is time to drive the system through the offset distances of m and n, location data is tested dynamically by means of a comparator 54.

Assume an arbitrary cross hair location in the register for the x dimension of 100,000 microns. Assume further that the offset is 86,000 microns. The register has a first or beginning value, and this value is duly noted. In this example, it will be 100,000 microns. Knowing that the offset is 86,000 microns, the comparator 54 compares the dynamic value in the register 52 with the desired end value, 186,000 in this instance. The position selector is operated, and the pulse driver forms appropriate pulses, supplied to the stepping motor 21. Simultaneously, the register increments toward the desired value or 186,000 microns. When a comparison is achieved. a signal is given to the position selector 51 which switches off. At this juncture, translation has been fully perfected. Of course, it is also accomplished in the second dimension. This is accomplished in the same fashion.

This process locates the stylus tip 28 over the particular fiber 40. Then, the z stepping motor 56 is operated through the similar gear box 57 to provide translation in the z direction. The gear box for the z direction is connected with the stage 20 also. As will be understood, the stage 20 is movable in all three dimensions. The pulse driver 50 forms pulses which are output to a recorder 60. The recorder 60 is connected with the load cell output device 25. The recorder records two data, namely the translation in the z direction at multiple locations and records the loading from the load cell at each location. Thus, the tip 28 may penetrate slowly as is it is advanced. This might require several measurements at several different depths of penetration. That penetration is recorded opposite a particular load value. The recorder 60 is preferably provided with the locations of the various fibers that have been tested. Thus, if 500 fibers are tested, and each fiber has 50 sets of data, a very substantial body of data is then provided. This enables the testing of multiple fibers with multiple depths of penetration of the tip 28.

In the foregoing description, it will be understood that the location of the optical axis coincides with the x-y coordinates, thereby defining an origin of 0,0. This origin, of course, can be moved for each test. In other words, a single fiber can be tested at an arbitrary point in the specimen which point defines the origin at 0,0. On the other hand, fibers can be tested by selecting fibers in a specified pattern, for instance those which are near the center and those which are near the outer edge of the specimen 30. If this is the case, the location of the individual fibers may be important and to this end, the x-y coordinate measurements of locations from fiber to fiber may be important.

A preferable method of use has been described above. It is assisted by incorporating the camera systems. This enables the photographing of the field of view with a still camera. Also, the video camera can be used to provide a very large screen image. It is possible through the use of a typical large television receiver to focus on an individual fiber which (measuring five microns in diameter) nevertheless presents an image on the screen of about one inch in diameter. This scaling up of the individual fibers enables the operator to more accurately zero the tip within the center of the fiber and to inspect the mode of breaking.

While the foregoing is directed to the preferred embodiment, the scope is determined by the claims which follow.

What is claimed is:

1. A method of testing the bond of reinforcing fibers in reinforced polymer composite members, the method comprising the steps of:
    (a) cutting a face on a composite member approximately perpendicular to reinforcing fibers in the composite member to expose fiber ends at the face;
    (b) locating up to N exposed fiber ends at the face where N is an integer wherein the fiber end location is identified relative to a reference;
    (c) moving a load applying member to a selected fiber end location to align the load applying member over the fiber end;
    (d) loading a fiber end at the face with a load applying member having an area of contact with the fiber end less than the area of the fiber and wherein the loading is controlled to achieve a specified load;
    (e) moving the load apply member between first and second positions along a path of travel directed toward the fiber end to accomplish penetration of the load applying member into the fiber;
    (f) measuring loading during penetration of the load bearing member into the composite member to obtain a measured value related to penetration; and
    (g) determining the reinforcing fiber bond as a function of measured penetration.

2. The method of claim 1 including the step of performing tests on composite members wherein the composite members are uniform in thickness, and are supported on a mounting member.

3. The method of claim 2 including the step of centering the load applying member relative to the reinforcing fiber.

4. The method of claim 3 including the steps of moving the load applying member along X and Y coordinates prior to testing to align the load applying member over the center of the fiber end.

5. The method of claim 1 including the step of controlling the load of the load applying member to obtain data from testing multiple reinforcing fibers.

6. The method of claim 5 wherein the load bearing member has a contact area smaller than the end of the fiber.

7. The method of claim 1 including the step of measuring load applying member penetration from a reference position prior to starting penetration.

8. The method of claim 7 including the step of measuring penetration and force during penetration applied to the load applying member.

9. The method of claim 8 including the step of measuring load applying member travel between initial contact with the fiber end and final penetration into the fiber end.

10. The method of claim 9 including the step determining reinforcing fiber bond for N fiber ends by repetitively making measurements at N fiber ends wherein each of the measurements is initially proceeded by movement of the load applying member in an X and Y defined rectilinear system to locate the fiber ends.

11. Apparatus for testing the bond between a small fiber in a polymer matrix, the apparatus comprising:
   (a) an optical microscope having an x, y defined origin within the field of view of the optical system, the optical system being scaled to provide a focus to view of the end of a fiber in a supportive polymer matrix;
   (b) a stylus having a tip positioned for testing of the bond between the fiber and polymer matrix, the tip being located from the x, y origin by offset distances of m and n;
   (c) means for supporting a small fiber in a polymer matrix for undergoing testing, said means supporting the small fiber in the optical field of view of said microscope; and
   (d) means for accomplishing relative movement between a specified fiber undergoing test and the optical microscope such that movement in the x and y dimensions is accomplished by travel through offsets of m and n, thereby locating a specified fiber viewed through the microscope system at a known location and positioned relative to the stylus tip for testing of embedment of the stylus tip at the specified fiber.

12. The apparatus of claim 11 wherein said movement means includes separate x and y stepping motors connected with gear box means for providing controlled incremental movement in the x and y dimensions.

13. The apparatus of claim 12 including a movable stage which is moved by said x and y stepping motors.

14. A method of testing the bond holding a reinforcing fiber in a supportive polymer matrix comprising the steps of:
   (a) shaping a test specimen to define a face thereon intersecting an end of a fiber held in the polymer matrix;
   (b) locating the end of the fiber with an optical system wherein the locating step references the located fiber to a reference indicia in the optical system;
   (c) positioning a pointed test instrument a fixed distance away from reference indicia wherein the distance is represented by measures m and n in a two coordinate measuring system;
   (d) relatively moving the specimen to the test instrument by measures m and n;
   (e) moving the test instrument against the specimen by movement approximating perpendicular to the specimen fiber end to controllably load the fiber; and
   (f) measuring fiber performance during loading.

15. The method of claim 14 wherein the fiber is pushed by point contact loading by the test instrument, and performance is measured by test instrument travel as a function of test instrument loading on the fiber.

16. The method of claim 14 including the step of reversing movement by -m and -n to restore the fiber to the original location after testing.

17. The method of claim 16 including the step of visually inspecting the fiber after testing.

18. The method of claim 14 including the step of moving the specimen on a movable stage toward the test instrument.

19. The method of claim 14 including the step of viewing the end of the fiber in alignment with a cross hair visible through the optical system.

20. The method of claim 19 including the step of moving the cross hair between alignment with a first fiber to a second fiber.

* * * * *